United States Patent [19]

Marks

[11] Patent Number: 5,256,152
[45] Date of Patent: Oct. 26, 1993

[54] SAFETY NEEDLE AND METHOD OF USING SAME

[76] Inventor: Lloyd A. Marks, 727 Great Springs Rd., Bryn Mawr, Pa. 19010

[21] Appl. No.: 850,959

[22] Filed: Mar. 11, 1992

Related U.S. Application Data

[63] Continuation-in-part of Ser. No. 783,925, Oct. 29, 1991.

[51] Int. Cl.⁵ .............................................. A61M 5/32
[52] U.S. Cl. ................................. 604/198; 604/192; 604/263; 128/919
[58] Field of Search ............... 128/919; 604/110, 192, 604/198, 263

[56] References Cited

U.S. PATENT DOCUMENTS

| | | |
|---|---|---|
| 3,134,380 | 5/1964 | Armao . |
| 4,139,009 | 2/1979 | Alvarez . |
| 4,725,267 | 2/1988 | Vaillancourt . |
| 4,735,618 | 4/1988 | Hagen . |
| 4,775,369 | 10/1988 | Schwartz . |
| 4,781,692 | 11/1988 | Jagger et al. . |
| 4,781,697 | 11/1988 | Slaughter ............................ 604/192 |
| 4,790,828 | 12/1988 | Dombrowski et al. . |
| 4,867,172 | 9/1989 | Haber et al. . |
| 4,887,998 | 12/1989 | Martin et al. ...................... 604/110 |
| 4,892,521 | 1/1990 | Laico et al. ......................... 604/192 |
| 4,897,083 | 1/1990 | Martell . |
| 4,898,589 | 2/1990 | Dolgin et al. . |
| 4,911,706 | 3/1990 | Levitt ................................... 604/198 |
| 4,915,697 | 4/1990 | DuPont . |
| 4,917,672 | 4/1990 | Terndrup et al. . |
| 4,921,490 | 5/1990 | Spier et al. ......................... 604/192 |
| 4,935,013 | 6/1990 | Haber et al. . |
| 4,950,250 | 8/1990 | Haber et al. . |
| 4,955,866 | 9/1990 | Corey ................................... 604/192 |
| 4,998,922 | 3/1991 | Kuracina et al. . |
| 5,051,109 | 9/1991 | Simon .................................. 604/263 |
| 5,061,250 | 10/1991 | Shields ................................ 604/198 |

*Primary Examiner*—C. Fred Rosenbaum
*Assistant Examiner*—Corrine Maglione
*Attorney, Agent, or Firm*—Wigman, Cohen, Leitner & Myers

[57] ABSTRACT

A safety hypodermic needle and a method of using the same are disclosed. The safety needle comprises a hypodermic needle and a protective sheath molded of an flexible polymeric material. The protective sheath comprises a needle cup which encloses the sharp needle point and is supported on a plurality of outwardly flexed ribs. The needle cup has a needle opening which is misaligned with the needle axis in the at rest or unflexed condition of the protective sheath. Application of transverse and axial forces to the needle cup aligns the needle with the opening and cause the ribs to bow outwardly so that the needle passes through the opening and into the patient's body.

26 Claims, 7 Drawing Sheets

SAFETY NEEDLE AND METHOD OF USING SAME

CROSS-REFERENCE TO RELATED APPLICATION

This application is a continuation-in-part of U.S. application Ser. No. 783,925 pending filed Oct. 29, 1991.

FIELD OF THE INVENTION

The present invention relates generally to hypodermic syringes and phlebotomy apparatus and more particularly to a safety hypodermic needle for disposable hypodermic syringes and phlebotomy apparatus and a method of using the safety needle to prevent inadvertent needle sticks or punctures.

Description of the Prior Art

Infectious diseases can be transmitted to medical personnel and others by way of inadvertent needle sticks or punctures with an infected needle of an hypodermic syringe or phlebotomy apparatus. Cases have been reported in which human HIV (AIDS) infection and other infectious diseases have been transmitted by accidental or inadvertent needle sticks. A number of devices have been developed for the purpose of preventing such needle sticks.

One prior art device comprises a spring-biased tube located within the lumen of the needle. After the needle has been used, the tube is advanced by the spring beyond the needle bevel point thereby protecting medical and other personnel from an inadvertent needle stick. This device is relatively complex, costly and reduces the effective lumen size of the needle.

Another type of prior art device in more common use employs a protective sheath external to the needle which is retractable to permit insertion of the needle into the body of the patient and is then slidable back over the needle past the needle point as, or after, the needle is withdrawn from the body. In some of this type of prior art protective device, a spring or axially resilient sheath is used to extend the sheath over the needle point upon withdrawal of the needle. Several of these prior art devices use a collapsible sheath formed by a plurality of resilient arms surrounding the needle. The arms are bowable or bendable outwardly away from the needle axis to expose the needle and are movable inwardly toward the needle axis to again enclose the needle within the sheath. Some of these devices require a positive step or a specific manual act by the phlebotomist or user to deploy the protective sheath after it is withdrawn from the patient's body. Still other devices are made from a plurality of parts making them more complex to manufacture and thus more costly to the consumer.

One of the primary shortcomings of the prior art devices which use protective sheaths of the foregoing type is that during at least some of the period of time between the preparation of the hypodermic syringe for an injection, or the phlebotomy apparatus for entering a vein, and the discarding of the used needle, inadvertent needle sticks of persons other than the patient are still possible because the needle is aligned with the opening in the protective sheath.

It would be desirable, therefore, to provide a safety hypodermic needle for use with a disposable hypodermic syringe, as well as for use with catheter needles and other types of body-penetrating hypodermic needles, that overcomes the foregoing limitations and shortcomings of the prior art devices, has a minimum number of parts and is economical to manufacture and easy to use. In particular, it would be highly desirable and advantageous to provide a safety needle that is operable to positively prevent exposure of the needle point at all times, except when the user brings the needle in close proximity to and directs the needle point at the location on the patient's body where the needle is to be inserted and inserts the needle at that location.

SUMMARY OF THE INVENTION

The present invention is directed to a safety needle and a method of using the needle to prevent inadvertent needle sticks. The safety needle of the invention comprises a needle, typically a hollow, hypodermic needle with a bevel point or tip, a collar into which the needle is inserted and a protective sleeve or sheath which is fixed at one end to the collar and at least partially encloses the greater part of the longitudinal extent of the needle and completely encloses the needle point until the needle is ready to be inserted in the body. The sheath is preferably molded in one piece of a suitable polymeric material, such as polyethylene, polypropylene or the like, and preferably a clear or transparent material. Other manufacturing techniques, such as extrusion, may be employed. The sheath may also be made of different materials, preferably polymeric materials, and assembled together in its final form.

The protective sheath has a generally tubular form, preferably with an elliptical cross-section, and comprises a first tubular portion, or mounting sleeve, that is fixed to or over the needle collar and a second tubular portion or needle cup that has an end cover and encloses the needle bevel point. A plurality of flexible ribs or slats extends between the first and second tubular portions. Each of the ribs has a curved cross-section arranged with a convex surface outwardly and a concave surface inwardly, hereinafter described as an outwardly convex cross-section.

When a force is applied axially to the sheath in a direction to compress the sheath, i.e., in a direction to move the first and second tubular portions toward one another, the ribs are constrained by their particular curvilinear shape to flex or bow outwardly away from the needle. The end cover of the second tubular member or needle cup is provided with an opening through which the needle is adapted to pass, when, and only when, it is aligned with the opening. In the "at rest" or unflexed condition of the molded protective sheath, that is, with no external forces acting on the sheath, the needle bevel point is misaligned with the end cover opening and confronts the end cover itself. Thus, if an axial compressive force is applied to the protective sheath (for example, as might accidentally occur if the hypodermic syringe to which the needle is attached were dropped or inadvertently brought into contact with the body of the person administering the injection or carrying out the phlebotomy procedure), the needle point does not pass through the end cover opening to cause a needle stick. Rather, the needle point is driven against the end cover thereby effectively protecting against inadvertent needle sticks. It is also contemplated by the present invention that the needle cup may be treated to alter its physical properties or may be molded of a polymeric material different from or thicker than that of the sheath, especially where the resiliency requirements of the flexible rib material are not compatible with the toughness requirement for the needle cup, e.g., to prevent penetration of the end cover by the sharp needle point. The needle cup may be made of metal or molded of a different plastic material and affixed to the end of the protective sheath by an adhesive, although other equivalent constructions are contemplated within the scope of the invention.

When it is desired to expose the needle to perform, for instance, a phlebotomy procedure, the user engages the skin of the patient with the protective sheath at a point adjacent the vein or vessel to be penetrated. The user then urges the sheath laterally against the skin in such a way as to apply a lateral force to the needle cup and flex the ribs to reposition the needle cup so that the opening in the end cover is aligned with the needle axis. The needle may then be urged forwardly through the opening and into the vein to be penetrated. As the needle is urged forwardly through the opening, the sheath is axially compressed against the skin and the ribs flex or bow outwardly until the proper needle penetration depth is reached. When the phlebotomy procedure is completed and the needle is withdrawn from the patient, the axial compressive force is removed and the sheath returns to its original unflexed condition in which the needle cup covers the needle point and the needle axis is again misaligned with the opening. In this way, a needle which is potentially contaminated with the body fluids of a patient carrying an infectious disease is rendered safe from the standpoint of needle sticks.

The safety needle of the invention can also be used in medical procedures for inserting catheters into blood vessels with a needle and in administering injections to patients with hypodermic syringes. One common technique for administering intramuscular injections involves insertion of the needle into the body in a "dart-like" manner by holding the syringe in one hand and propelling the hand toward the body with a short rapid stroke. Obviously, this technique for administering injections requires that the needle be exposed or unsheathed. For this purpose, the protective sheath of the present invention is provided with a tab or finger, preferably molded integrally with the cup between an adjacent pair of ribs. The tab has a length sufficient to be grasped and manipulated to first move the needle cup transversely in such a way that the needle is aligned with the end cover opening and then to axially compress or retract the sheath and flex the ribs outwardly thereby extending the needle through the opening. The syringe and tab may then be grasped in one hand and the injection procedure may be carried out in the conventional manner. Upon withdrawal of the needle, of course, the sheath returns to its unflexed condition whereby the needle cup axially extends over the needle and is repositioned so that the needle point is enclosed by the needle cup and misaligned with the end cover opening.

In other advantageous embodiments of the invention, especially for administering injections with hypodermic syringes, the above-described tab or finger, which is integrally molded to the protective sheath, may be provided with means for "cocking" or latching the protective sheath in the unsheathed condition with the ribs flexed outwardly and the needle exposed. Such latching means preferably comprises one or more holes in the tab or finger and a hook or pin affixed to or integrally formed with the first tubular portion or mounting sleeve of the protective sheath. According to these embodiments of the invention, the tab or finger may be grasped and manipulated as described above to retract the sheath, thereby flexing the ribs outwardly and extending the needle through the opening in the needle cup. Then, the tab is pressed against the hook on the mounting sleeve so that one of the holes in the tab engages over the hook to hold the sheath in its unsheathed condition with the needle exposed. Upon use of the needle, i.e., by administration of an injection, the tab is automatically or manually disengaged from the hook and when the needle is withdrawn from the patient, the protective sheath will be returned to its unflexed or protective position with the needle cup enclosing the used needle tip as described above.

Several additional embodiments of the invention are disclosed including an embodiment in which the needle cup and ribs may be flexed transversely away from the needle point and latched with the needle point exposed. This embodiment is also especially suitable for use in inserting an indwelling catheter in a blood vessel.

In another embodiment of the invention, the needle cup comprises two portions hingedly connected together such that the portion confronting the needle point may be pivoted away from the needle point to expose the needle point for administering an injection. According to a further embodiment of the invention, the protective sheath has a rectangular cross-section for enclosing the needle and needle point.

Although a number of embodiments of the safety needle of the invention are disclosed in the specification and accompanying drawings, it should be understood that, apart from the specific embodiments disclosed herein, this invention is generally applicable to any type of hypodermic needle used to penetrate the body to either introduce a substance into the body or to withdraw a substance, such as blood or other body fluids, from the body.

With the foregoing and other objects, advantages and features of the invention that will become hereinafter apparent, the nature of the invention may be more clearly understood by reference to the following detailed description of the invention, the appended claims and to the several views illustrated in the attached drawings.

DETAILED DESCRIPTION OF THE INVENTION

Figure 1:
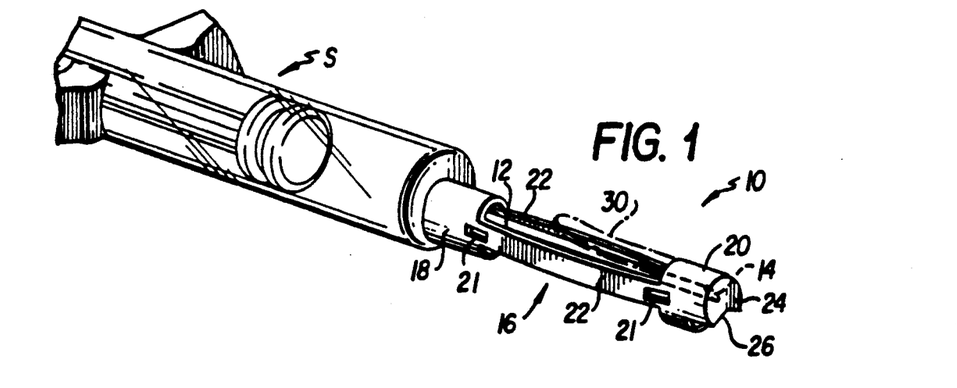
FIG. 1 is a fragmentary perspective view showing a hypodermic syringe employing one embodiment of the safety needle of the invention.
Figure 2:
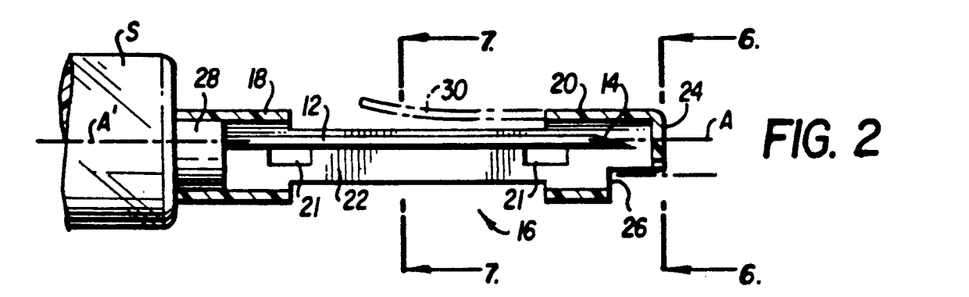
FIG. 2 is a side elevation view, in cross-section, of the safety needle of FIG. 1.

Referring now in detail to the drawings, there is illustrated in FIGS. 1 and 2 an hypodermic syringe S employing one embodiment of the safety needle apparatus of the present invention which is designated generally by reference numeral 10. The safety needle 10 comprises a conventional hollow steel hypodermic needle 12 having an axis A and a sharp beveled point or tip 14 for puncturing the skin. The needle 12 and its tip 14 are enclosed in a unitary protective sleeve or sheath 16 having a generally elliptical cross-section and preferably molded in one-piece of a clear, flexible polymeric material, such as polyethylene, polypropylene or the like.

Sheath 16 comprises a first tubular member or mounting sleeve 18 and a second tubular member or needle cup 20 connected by a plurality (two in this embodiment) of outwardly flexible or bowable ribs or slats 22 which in their normally unstressed or "at rest" condition maintain the tubular members 18, 20 in generally coaxial relationship. Second tubular member or needle cup 20 has an end cover 24 with a needle opening 26. The needle opening 26 is formed by cutting away a generally V- or pie-shaped portion of the end cover 24 and a portion of the wall of needle cup 20 so that the opening 26 is offset from the major axis of the elliptical cross-section of the sheath and misaligned with the needle axis A. Other configurations of the needle opening 26 are also contemplated, e.g., an opening or bore in the end cover 24 only, which opening or bore may be circular, triangular or any other appropriate shape. It is also contemplated that the needle cup 20 may be formed in other ways and have other shapes. For example, the closed end of the needle cup may be formed by heat sealing the end of the tubular member from which the needle cup is formed along the major axis of the elliptical or oblong cross-section thereof. Similarly, it is also contemplated that instead of the ribs or slats 22, the connection between the first and second tubular members 18, 20 could have other forms, such as a helical spring, a multiple helix, spiral structure or the like, which will provide a lateral offset and be sufficiently resilient to be laterally flexed as well as axially compressed. An axially compressible bellows structure could also be employed as a connection between the first and second tubular members, especially where the working space is limited, such as in the mouth of a patient.

As best seen in FIG. 2, the axis A of needle 12 is preferably coincident with the axis A' of syringe S. The syringe S has a hub or collar 28 the axis of which is offset from, i.e., eccentric to, the axes A,A'. Thus, when the first tubular member 18 of sheath 16 is mounted on the collar 28 of the syringe, the sharp needle point 14 is disposed in confronting relation with the end cover 24 and the needle 12 is misaligned with the needle opening 26. This is the normal unstressed or "at rest" condition of the sheath 16 and it will be appreciated by those skilled in the art that in this condition the likelihood of an inadvertent needle stick from needle 12 is remote. For instance, if the safety needle were inadvertently pushed axially against a person's body, the needle tip 14 would engage the inside surface of end cover 24 and prevent a needle stick. As will be understood from the description which follows, an initial transverse force must be applied to the needle cup 20 to align the needle 12 with the needle opening 26 before the needle can pass through the opening.

Shown in phantom lines in FIGS. 1 and 2 is a flexible tab or finger 30 which may be optionally provided on the sheath 16. Preferably, when provided, the tab 30 is molded integrally to the rearward edge of the second tubular member or needle cup 20 between the two ribs 22 and extends approximately two-thirds of the distance between the tubular members 18,20. In addition, the tab 30 is preferably curved slightly upwardly as shown to prevent possible engagement of the tab with tubular member 18 when the arms 22 flex outwardly as described hereinafter. As will be explained in more detail, the tab 30 is primarily useful when the hypodermic syringe S is to be used to administer an intramuscular injection to a patient, although it could also be used if desired or convenient during a phlebotomy procedure to unsheath the needle 12 prior to insertion of the needle into a blood vessel.

Although only two flexible ribs 22 are shown, it should be understood that a greater number of ribs may be used. It is also possible according to the invention to construct the sheath 16 with only one rib and still achieve the purpose and function of the invention. Other equivalent arrangements of the ribs will be apparent to those of skill in the art in light of the teachings herein.

Figure 6:
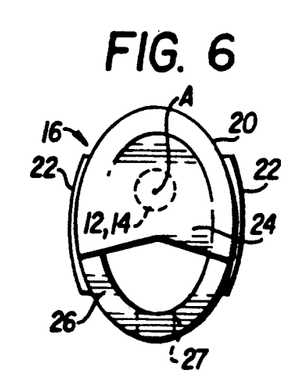
FIG. 6 is an end view of the safety needle taken along line 6—6 in FIG. 2.

Referring now to FIG. 6, there is shown an end view of the sheath 16 in its at rest or unflexed condition looking toward the end cover 24 of the needle cup 20 and showing the relative positions of the needle 12 and the needle opening 26. As seen in FIG. 6, the sheath 16 has a generally elliptical cross-section. For a given cross-sectional area, an elliptical or oblong shape of the sheath advantageously permits a greater spacing between the axis A of the needle 12 and the proximate edge of the needle opening 26. While an elliptical or oblong cross-section of the sheath is preferred, other cross-sectional shapes are possible, including circular, polygonal and the like.

Also shown by the dashed lines in FIG. 6 is an optionally provided slot 27 having a width substantially equal to the diameter of the needle 12 and extending the longitudinal length of the lower side of the needle cup 20. Such a slot may be especially useful in connection with a catheter as shown in FIGS. 13–17.

Figure 7:
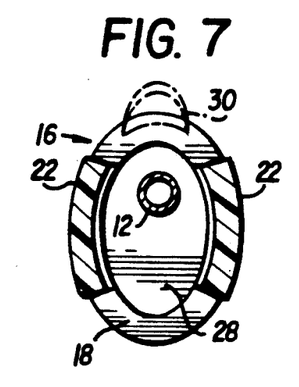
FIG. 7 is a transverse cross-sectional view of the safety needle of the invention taken along line 7—7 in FIG. 2.

FIG. 7 illustrates the cross-sectional shape of the ribs 22, the outer surfaces of which are convex and the inner surfaces of which are concave. The cross-sectional shape, area and thickness of the ribs are important in determining the magnitude of the force required to cause the rib to deflect or bow outwardly. It is also important according to the invention that the ribs 22 be designed or configured to reliably bow outwardly rather than inwardly when the appropriate axial force is applied to the protective sheath 16. The particular curvature of the ribs shown in FIG. 7, i.e., outwardly convex, tends to cause each rib to bow outwardly in the desired direction (FIG. 5), rather than inwardly toward the needle as it might, for instance, if the rib cross-section were planar or inwardly convex. Other factors may affect to some extent the tendency of the ribs to bow outwardly and the axial force required to initiate bowing, such as, for example, the type of material from which the sheath is made, the radius of curvature, thickness and circumferential length of the ribs, etc.

Figure 8:
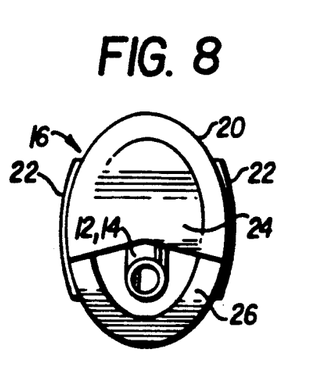
FIG. 8 is an end view of the safety needle of the invention taken along line 8—8 in FIG. 3.

Outward bowing can be insured by other means as well. As best illustrated in FIGS. 6–8, the ribs 22 in the "at rest" condition are provided with a slight outward deflection at the approximate midpoint of the length of each rib. Such a slight initial outward deflection will insure that the ribs will bow outwardly upon the application of axial force in virtually all cases. Another means to insure outward bowing of the ribs is the provision of cutouts 21 (FIGS. 1–4) in the regions where the ribs 22 join the tubular members 18, 20. Other possible means include the provision of notches (not shown) on opposite edges of the ribs at the midpoint of the rib length.

Figure 3:
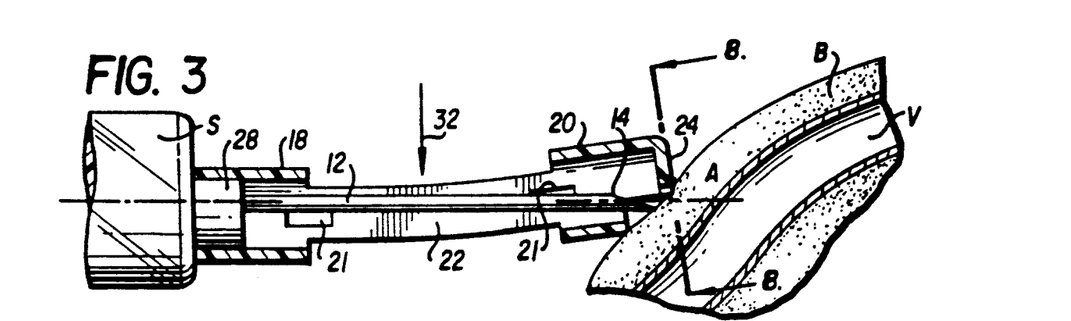
FIG. 3 is a side elevation view, in cross-section, illustrating the initial position of the safety needle when used in a phlebotomy procedure.

Referring now to FIGS. 3–5 and 8, the method of using the safety needle of the invention will be described in relation to a phlebotomy procedure. From the at rest or unflexed condition of the sheath shown in FIG. 2, the phlebotomist engages the body B of a patient adjacent a blood vessel V with the region of the needle cup 20 surrounding the needle opening 26, i.e., the lower portion of the cup 20 as viewed in FIG. 8. Then, the needle cup 20 is pressed against the body, i.e., in the direction shown by the arrow 32 in FIG. 3, until the needle point 14 is aligned with the needle opening 26 as shown in FIGS. 3 and 8 and the ribs 22 are flexed slightly upwardly as shown.

Figure 4:
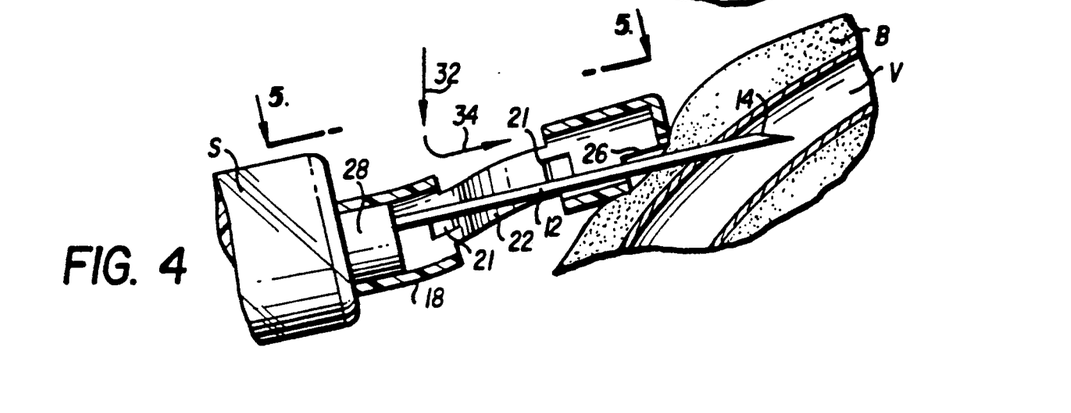
FIG. 4 is a side elevation view, in cross-section, illustrating another position of the safety needle during the phlebotomy procedure.
Figure 5:
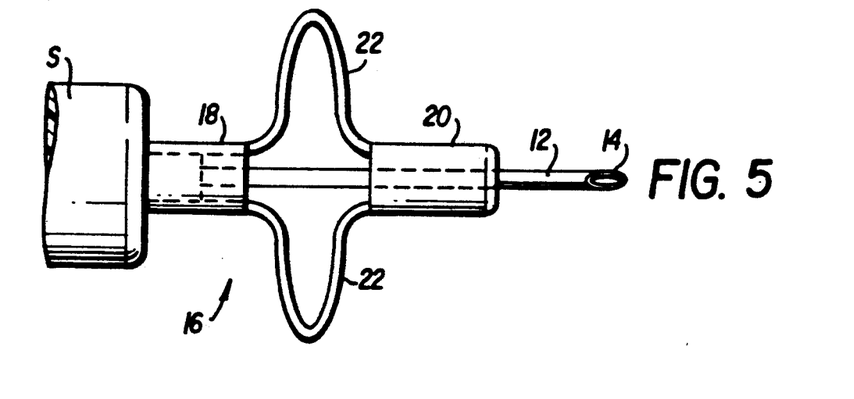
FIG. 5 is a top view of the safety needle of FIG. 4 as viewed from the position shown by the line 5—5 in FIG. 4.

From the position shown in FIG. 3, the phlebotomist advances the syringe S axially in the direction of the arrow 34 in FIG. 4 until the needle point 14 penetrates the skin of body B and passes into the blood vessel V. Advancement of the syringe S results in an axial compression force being applied to the sheath 16 which, in turn, causes the ribs 22 to flex or bow outwardly as shown in FIG. 5. Preferably, the polymeric material of the sheath 16 is clear or transparent so that the position and advancement of the needle 12 and needle point 14 can be visually monitored by the phlebotomist during the procedure.

After the phlebotomy is completed, i.e., after blood from the vessel is drawn into the syringe and the needle is withdrawn, the sheath returns to its at rest or unflexed condition shown in FIG. 2 via the FIG. 3 position. In the FIG. 2 position, the needle 12 and needle point 14 are again in a safe position with the needle point 14 confronting the end cover 24. It will be appreciated, therefore that the needle point 14 is always enclosed in a safe position in needle cup 20, except during the time the needle 12 is actually in the process of being advanced into or withdrawn from the body.

If the hypodermic syringe S is to be used to administer an injection by a procedure in which the needle is unsheathed prior to contacting the skin with the sheath, the tab 30 (shown in phantom in FIGS. 1, 2 and 7) may be grasped by the user and pulled transversely of the needle axis A to deflect the sheath to the position shown in FIG. 3. The tab 30 is then pulled toward the syringe S until the sheath 16 is in the position shown in FIGS. 4 and 5 with the needle 12 exposed or unsheathed. In this position, the tab 30 may be placed against the syringe or the first tubular member 18 and gripped by the same hand which grips the syringe to administer the injection. While greater care must be used to avoid inadvertent needle sticks in this procedure because the needle is exposed during part of the procedure, such inadvertent sticks as may occur are not as dangerous because the needle has not been contaminated with potentially infectious body fluids. On the other hand, after the needle is inserted in the body, the tab 30 is released so that when the injection is administered and the needle is withdrawn, the protective sheath provides the same protection from inadvertent sticks as it provides for the phlebotomy procedure shown in FIGS. 3 and 4.

The tab 30 provides means for manually flexing the sheath to align the needle 12 with the needle opening 26 and for flexing the ribs 22 outwardly to unsheath or expose the needle 12. The tab 30 may have other equivalent forms and perform the same function.

Figure 9:
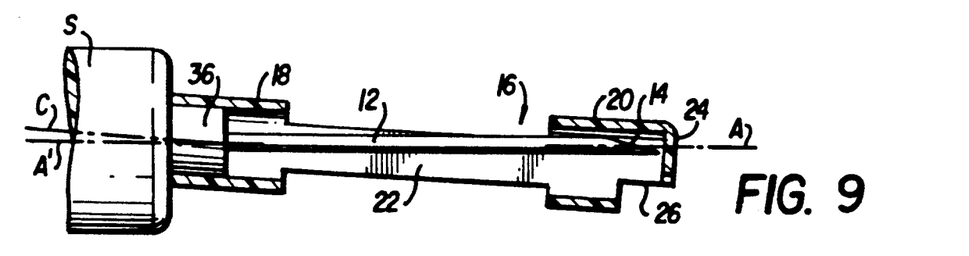
FIG. 9 is a side elevation view, in cross-section, of an alternate embodiment of the safety needle of the invention.

Referring now to FIGS. 9–11, several alternate, but equivalent, embodiments are shown for effecting the desired misalignment of the needle and the needle opening in the protective sheath when the sheath is in an at rest or unflexed condition. In FIG. 9, the sheath 16 may be identical to the sheath of FIGS. 1-8. The axis A of needle 12 and the axis A' of syringe S are coincident. However, the collar or hub 36 on which the first tubular member or mounting sleeve 18 is mounted has an axis C which is inclined to the axes A,A' so that when the mounting sleeve 18 is disposed over the collar 36, the sheath 16 is also inclined to the needle axis A and causes the needle point 14 to lie in confronting relation with the end cover 24 in generally the same position as shown in FIG. 2.

Figure 10:
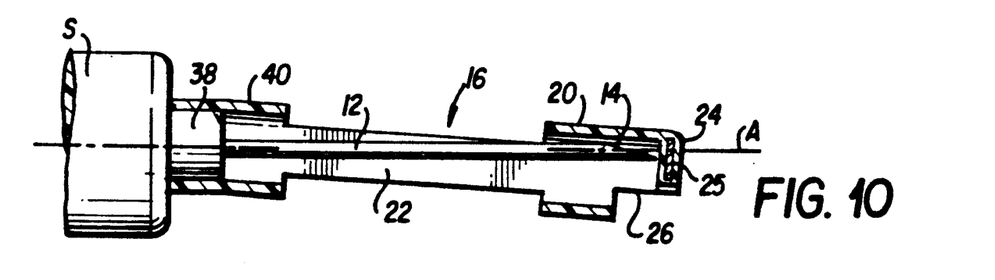
FIG. 10 is a side elevation view, in cross-section, of another alternate embodiment of the safety needle of the invention.

FIG. 10 illustrates another embodiment in which the syringe S, the collar 38 and the needle 12 have coincident axes. The mounting sleeve 40, however, has an angle or bend which results in an inclination of the protective sheath 16 from the point of the bend. This arrangement also positions the needle point 14 generally in the same protected location in the needle cup 20 as in the FIG. 2 embodiment. FIG. 10 also illustrates another alternative construction of the protective sheath of the safety needle of the invention. In the event the molded polymeric material of the needle cup of the sheath is not sufficiently thick or tough to prevent penetration of the end cover 24 by the needle point 14, the end cover may be molded with a metal or rigid plastic insert 25 to positively prevent needle penetration of the end cover 24.

Figure 11:
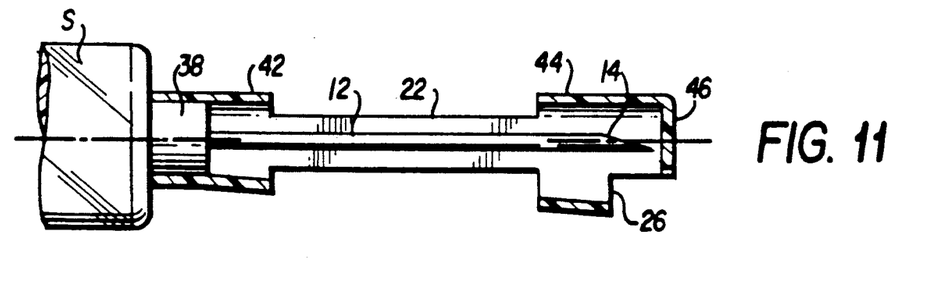
FIG. 11 is a side elevation view, in cross-section, of a further embodiment of the safety needle of the invention.

The FIG. 11 embodiment is a slight variation of the FIG. 10 embodiment in which the elliptical cross-sectional area of the sheath gradually increases from the collar 38 to the end of the needle cup 44 to form an elliptical conical shape with an enlarged end cover 46 which confronts the needle point 14. Other equivalent constructions of the sheath and syringe components to provide for misalignment of the needle 12 and needle point 14 with the needle opening 26 will occur to those skilled in the art in view of the teachings herein.

Figure 12:
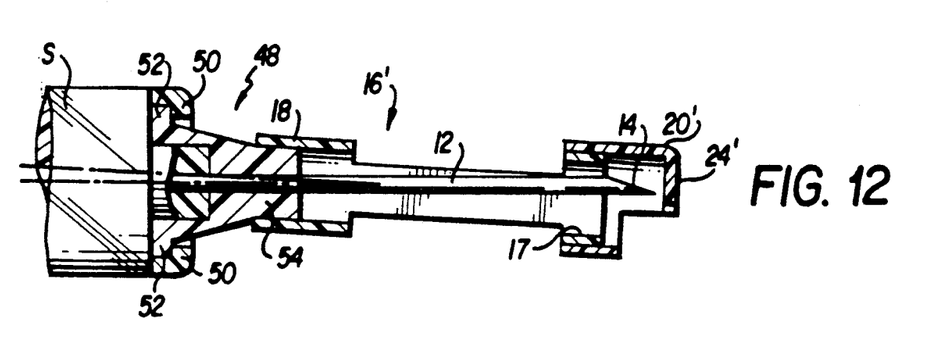
FIG. 12 is a side elevation view, in cross-section, of an embodiment illustrating an alternate embodiment of the needle cup and how the safety needle of the invention may be adapted to various forms of syringes with detachable needle mechanisms.

FIG. 12 illustrates an embodiment in which the safety needle device or protective sheath 16' of the invention has a needle cup 20' formed of a material different from the polymeric material of the sheath 16'. The needle cup 20' has a construction substantially identical to that of cup 20 shown in FIGS. 1-8. Cup 20' may be made of a metal, such as steel or aluminum, or it may be made of a polymeric material having different physical characteristics than the polymeric material of the sheath 16'. For example, the cup 20' could be made of a rigid plastic material to prevent penetration of the end cover 24' by the needle point 14. The cup 20' may be bonded or otherwise affixed to the tubular portion 17 which is molded integrally with the sheath 16'.

Also shown in FIG. 12 is an arrangement in which the protective sheath 16' is detachable from the syringe by a locking means. The locking means may comprise a quick-release or bayonet-type mechanism 48 comprising locking fingers 50 on the syringe and interengaging flange segments 52 on a conical adapter 54 which carries the needle 12 and sheath 16'. Other needle locking means are also contemplated by the present invention.

Figure 13:
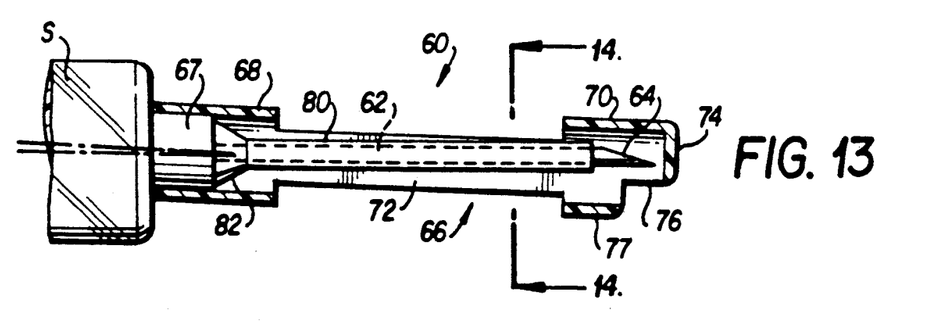
FIG. 13 is a side elevation view, in cross-section, of another embodiment of the invention that can be used to insert a tubular catheter into a blood vessel.
Figure 14:
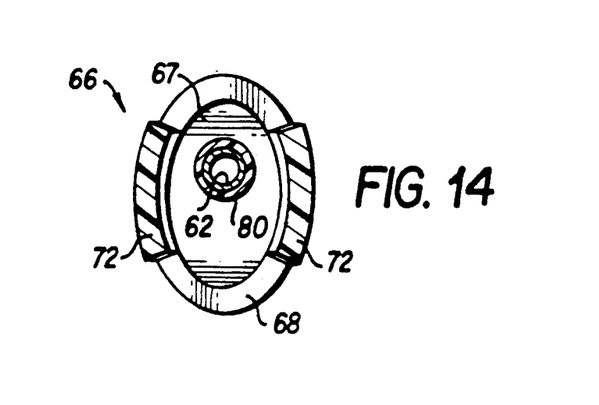
FIG. 14 is a cross-sectional view of the safety needle of FIG. 13 taken along line 14—14 of FIG. 13.

FIGS. 13-17 disclose an embodiment of the invention that may be used to insert a short indwelling catheter in a blood vessel. Referring first to FIGS. 13 and 14, an hypodermic syringe S is provided with the safety needle device 60 of the invention. In this case, the device 60 comprises a needle 62 with a needle point 64 enclosed by a protective sheath 66 mounted to a collar 67 of the syringe by a mounting sleeve 68. The needle point 64 is enclosed by a needle cup 70 which is connected to the mounting sleeve 68 by a plurality of ribs 72. Needle cup 70 has an end cover 74 which confronts needle point 64 and an opening 76 is provided in the lower portion of the needle cup 70. The bottom side 77 of the needle cup 70 may be provided with a slit or slot similar to the slit 27 shown in FIG. 6 for a purpose to be described.

A conventional flexible catheter tube 80 having a rigid plastic fitting or hub 82 is slidably disposed over the needle 64 which may have an anti-friction coating or sleeve on its exterior surface. The sheath 66 is similar in many respects to the sheath 16 of FIGS. 1-9 except that the opening 76 is sufficiently large to accommodate passage therethrough of the catheter 80 and its rigid plastic hub 82.

Figure 15:
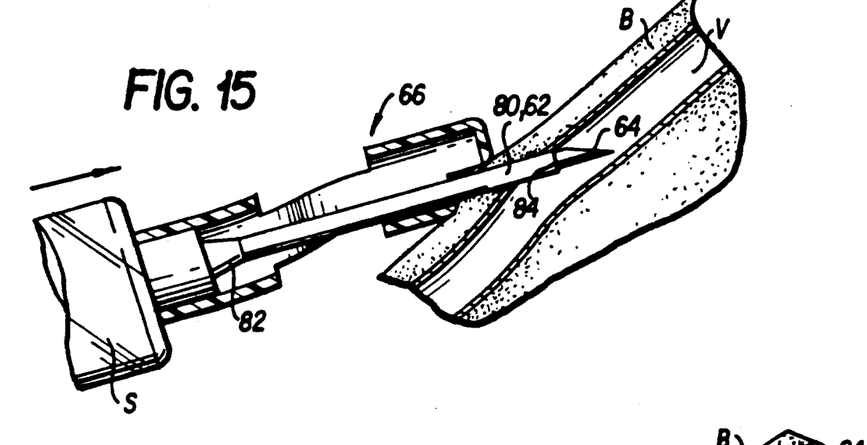
FIGS. 15-17 are side elevation views, in cross-section, illustrating the manner in which a catheter may be inserted in a blood vessel using the safety needle of FIGS. 13-14.
Figure 16:
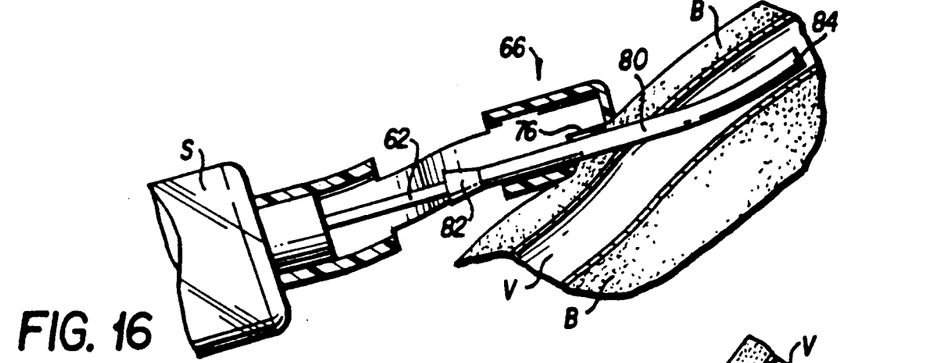
Figure 17:
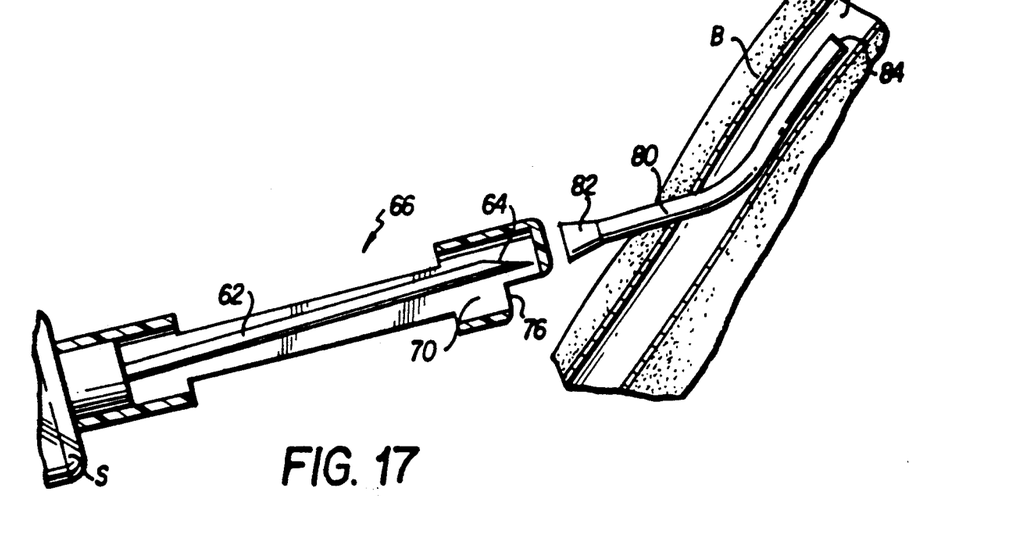

Referring to FIGS. 15-17, the safety needle device 60 is used in the following manner. The needle 62, together with the overlying catheter tube 80, is inserted into the blood vessel V of a body B in the same manner as shown and described above in connection with FIGS. 3-5. When the needle point 64 and the forward end 84 of the catheter 80 are located in the vessel V (FIG. 15), the catheter 80 and/or the hub 82 are advanced into the blood vessel V by sliding the catheter 80 axially along the needle 62 through the opening 76 (FIG. 16) until the hub 82 passes through the opening 76. If a slit (such as slit 27 in FIG. 6) is provided in the bottom side 77 of the needle cup 70 the passage of the hub 82 through the opening 76 will be facilitated. The syringe S is then withdrawn until the needle 62 pulls out of the catheter hub 82 and the protective sheath 66 returns to its at rest or unflexed position with the needle cup 70 covering and protecting the needle point 64 (FIG. 17). The catheter 80 remains positioned in the blood vessel.

The embodiment of the safety needle device 10' of the invention as shown in FIGS. 18-21 relates to an alternate construction of the protective sheath 16 in which a "cocking" or latching mechanism is provided on the sheath 16 for retaining the sheath in a position in which the needle is at least partially unsheathed until the latching mechanism is released by engagement with the body of a patient. Unless otherwise described, the components of the device 10' having the same reference numerals as the corresponding components of the embodiment of FIGS. 1-8 function in the same manner as in that embodiment and will not be described further herein.

Figure 18:
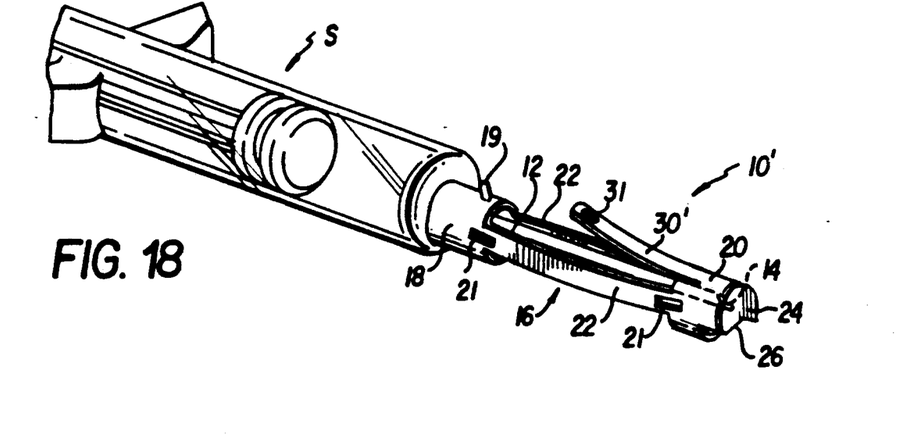
FIG. 18 is a fragmentary perspective view showing a hypodermic syringe employing another embodiment of the safety needle of the invention with a sheath latching mechanism.

Referring first to the perspective view of FIG. 18, it will be seen that the sheath 16 is provided with an integral tab or finger 30' similar to tab 30. Tab 30' has at least one elongated opening 31 adjacent the free end thereof. First tubular member 18 is provided with a preferably integrally-formed pin or hook 19 having a slight rearward inclination, i.e., toward the syringe S. The pin or hook 19 may also comprise a separate part that is molded or otherwise embedded in the material of the first tubular portion or sleeve 18. As in the embodiment of FIG. 1, the tab 30' preferably has an upward curvature for a purpose to be hereinafter described.

Figure 19:
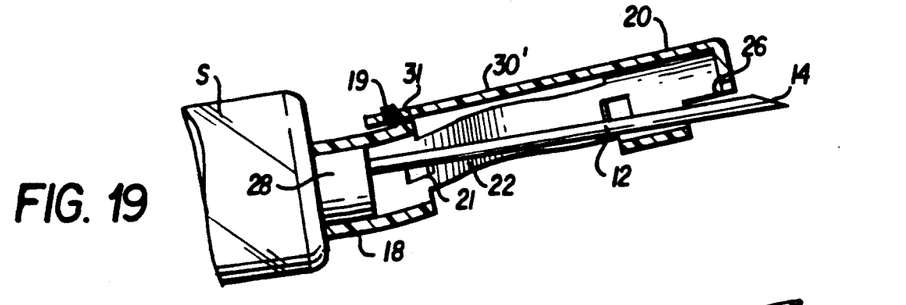
FIG. 19 is a side elevation view, in cross-section, of the safety needle of FIG. 18 with the latching mechanism engaged.

To engage the latching mechanism, the user of the syringe S grasps the tab 30' and pulls it upwardly and rearwardly toward the syringe S to flex the ribs 22 outwardly and partially unsheath the needle 12. When pulled sufficiently to the rear, the opening 31 in tab 30' is engaged over the pin 19 as shown in FIG. 19 and the tab 30' is released. In this position (FIG. 19), the needle point 14 is visible to the user and the needle 12 is partially unsheathed for administration of an injection.

Figure 20:
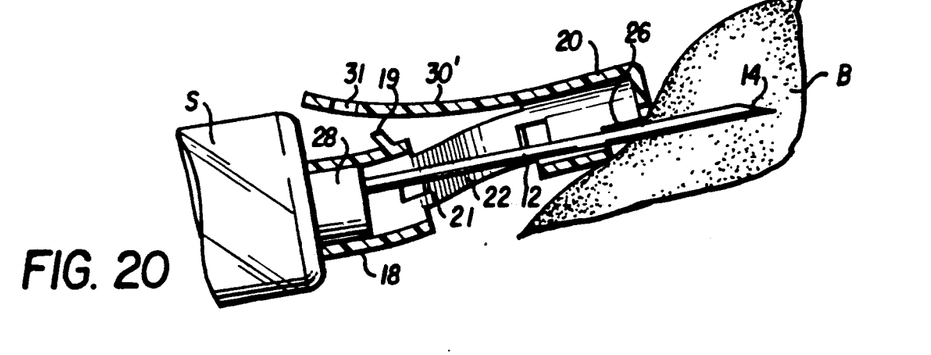
FIG. 20 is a side elevation view, in cross-section, of the safety needle of FIG. 18 illustrating the disengagement of the latching mechanism during a hypodermic injection procedure.

Administration of the injection with the safety needle device 10' is illustrated in FIG. 20. As the needle 12 penetrates the patient's body B, the needle cup 20 engages the body causing the needle cup 20 to be urged or moved rearwardly toward the syringe S. Such rearward movement disengages the opening 31 in tab 30' from pin 19 and the upward curvature of the tab 30' will cause the tab 30' to "spring" upwardly to the position shown in FIG. 20 thereby releasing the latching mechanism.

Figure 21:
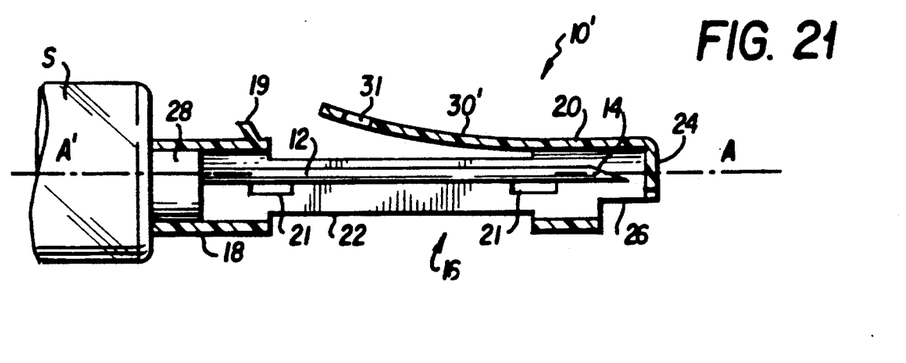
FIG. 21 is a side elevation view, in cross-section, of the safety needle of FIG. 18 showing the position of the safety needle after withdrawal of the needle from the patient following the injection procedure shown in FIG. 20.

Upon complete withdrawal of the needle 12 from the patient's body, the protective sheath 16 will return to its normal unflexed condition shown in FIGS. 18 and 21 with the axis A of needle 12 aligned with the end cover 24 of the needle cup 20, thereby protecting against inadvertent needle sticks.

It will be appreciated that other equivalent latching mechanisms may be used to releasably latch or "cock" the protective sheath of the invention in the position shown in FIG. 19 with a portion of the needle 12 exposed beyond the needle cup 20. It would be possible, for example, to locate the tab 30' on the mounting sleeve 18 and the pin on the needle cup 20. According to the invention, such latching mechanisms are releasable either manually or automatically by engagement of the protective sheath with the body of a patient.

Figure 22:
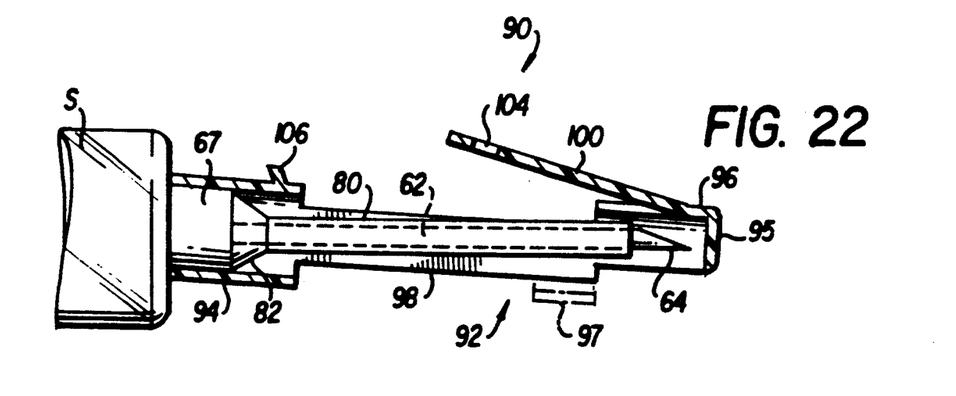
FIG. 22 is a fragmentary side elevation view, in cross-section, of another embodiment of the safety needle of the invention for inserting an indwelling catheter.
Figure 23:
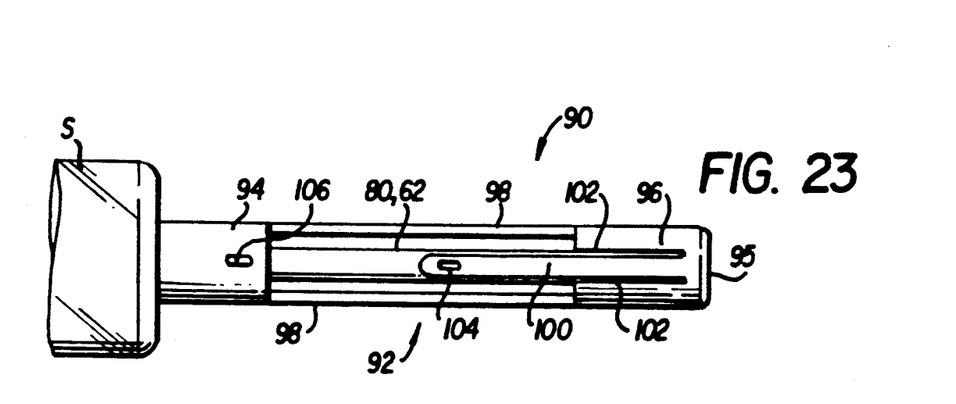
FIG. 23 is a top plan view of the safety needle shown in FIG. 22.
Figure 24:
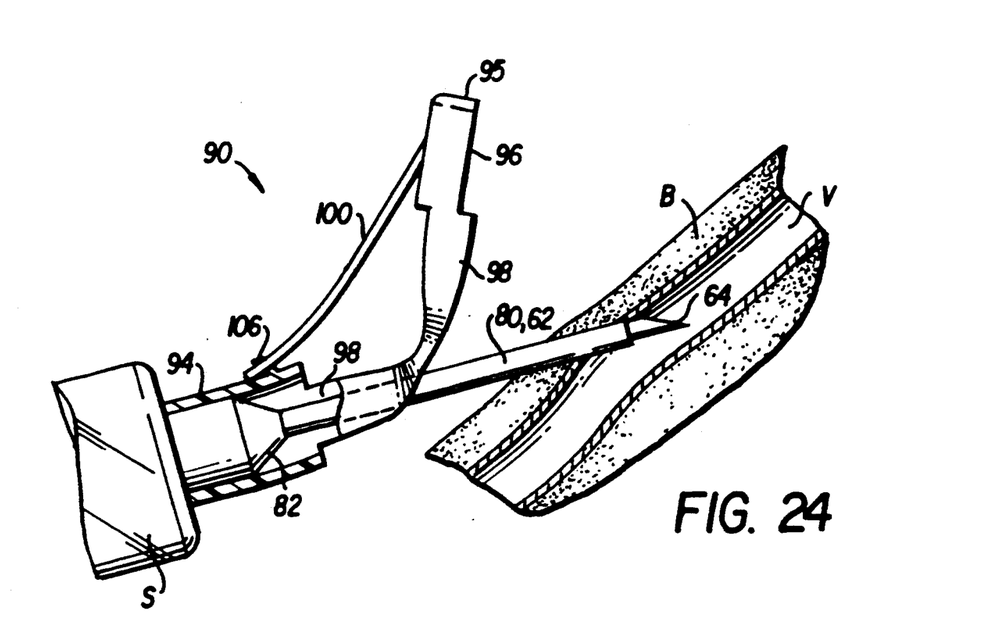
FIG. 24 is a side elevation view, partly in cross-section, illustrating the latched position of the protective sheath of FIGS. 22 and 23.

Another embodiment of the invention is shown in FIGS. 22-24 which also includes a cocking or latching mechanism similar to that of FIGS. 18-21 This embodiment is especially suitable for use with a syringe S that is used to insert an indwelling catheter 80 in a blood vessel. Since the conical hub 82 of the catheter 80 may have a relatively large diameter at its base, it is possible that the size of the normally provided opening in the needle cup (e.g., the opening 76 in needle cup 70 of FIG. 13) may be too small to provide easy passage of the hub 82. While the bottom slot 27 (FIG. 6) in the needle cup may provide one solution to this problem, the embodiment of FIGS. 22-24 provides additional solutions to the same problem in a safety needle device 90 with a latching mechanism.

Referring first to FIGS. 22 and 23, the safety needle device 90 is provided on a syringe S and comprises a needle 62 with a needle point 64 enclosed by a protective sheath 92 mounted to a collar 67 of the syringe S by a mounting sleeve 94. The needle point 64 is enclosed by a needle cup 96 which is connected to the mounting sleeve 94 by a plurality of ribs 98. Needle cup 96 has an end cover 95 which confronts needle point 64. The entire lower portion of the needle cup 96 is cut away to facilitate passage of the catheter 80 and catheter hub 82 through the protective sheath 92.

It is also within the scope of the invention that the ribs 98 may be connected between their lower edges with an arcuate or cylindrical portion or loop 97 shown in dashed lines in FIG. 23. Arcuate portion 97 will maintain the ribs 98 generally colinear with the needle 62 and catheter 80 during insertion of the needle and catheter into a blood vessel in a manner similar to that shown in FIGS. 15-16.

The latching mechanism for the embodiment of FIGS. 22-24 comprises a tab 100 formed integrally with the needle cup 96 and extending at a slight upward inclination rearwardly from the needle cup. As best seen in FIG. 23, the tab 100 is connected near the forward end of the needle cup 96 near the end cover 95. This structure is provided by the narrow slots 102 integrally formed in the needle cup 96 which also renders the needle cup more outwardly flexible or expandable. Adjacent its free end, tab 100 is provided with an opening 104. Integrally formed on mounting sleeve 94 is a pin or hook 106 having a slight rearward inclination.

In the unflexed position of the protective sheath 92 shown in FIGS. 22 and 23, the needle point 64 confronts the end cover 95 of needle cup 96 so as to protect against inadvertent needle sticks. When it is desired to use the safety needle device 90, the latching mechanism may be engaged by pulling the tab 100 upwardly and rearwardly toward the syringe S and by locating the opening 104 over the pin 106 on the mounting sleeve 94. This manipulation of the tab 100 causes the ribs 98 to flex generally upwardly to the position shown in FIG. 24 so that the needle cup 96 and the forward portion of the ribs 98 extend generally at right angles to the longitudinal axis of the needle 62 and catheter 80. In this position (FIG. 24), the needle point 64 is visible to the user and the needle is partially unsheathed for insertion of the catheter and needle into a blood vessel V in the manner described above in connection with FIGS. 15-17.

After the catheter 80 has been inserted into the vessel V and the syringe S and needle 62 are ready to be withdrawn from the patient's body B, the latching mechanism may be released by any slight rearward movement of the needle cup 96 which causes disengagement of the opening 104 from the pin 106. The needle cup 96 and ribs 98 will then flex forwardly and downwardly so that as the needle is withdrawn from the hub 82 of catheter 80 the needle cup and ribs will return to their normal unflexed position shown in FIGS. 22-23 with the end cover 95 in protective confronting relationship with the needle point 64 to thereby prevent inadvertent needle sticks.

Figure 25:
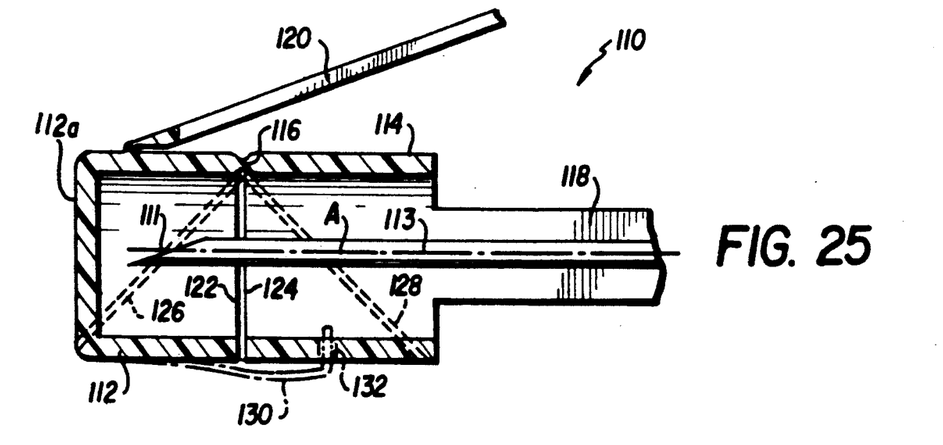
FIG. 25 is a fragmentary side elevation view, in cross-section, of another embodiment of the safety needle of the invention with the needle protected.
Figure 26:
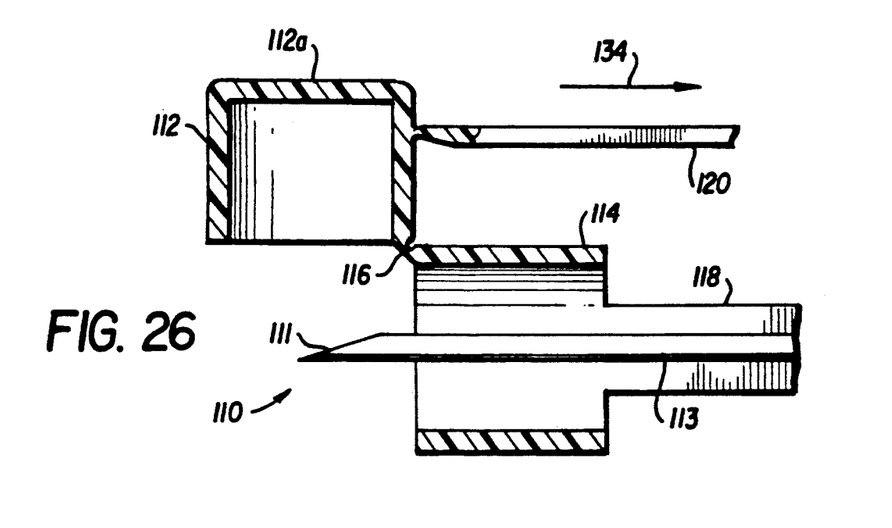
FIG. 26 is a fragmentary side elevation view, in cross-section, of the embodiment of the invention shown in FIG. 25 with the needle exposed.

FIGS. 25 and 26 illustrate another embodiment of the safety needle of the invention. In this embodiment, a protective sheath has a needle cup 110 integrally formed with a circular, elliptical or rectangular transverse cross-section with a front cup portion 112 and a rear cup portion 114. Front cup portion 112 has an end cover 112a and protectively encloses the needle point 111 of needle 113. The cup portions 112, 114 are hingedly connected by a so-called "living hinge" denoted by reference numeral 116. The needle cup 110 is connected to a mounting sleeve (not shown) similar to tubular member 18 (FIGS. 1-4) by means of one or more ribs 118. A tab 120 is integrally and hingedly formed on the front cup portion 112 adjacent the hinge 116 for a purpose to be described.

As shown in FIG. 25, the confronting edges 122, 124 of the cup portions 112, 114 are disposed substantially at right angles to the longitudinal axis A of needle 113. Alternatively, the confronting edges 122, 124 of the cup portions 112, 114 may be disposed at various angles to the needle axis A as shown by the dashed lines 126 and 128. Optionally, the front cup portion 112 may be releasably latched to the rear cup portion 114 by a flexible locking finger 130 formed on cup portion 112 and which engages in an opening 132 in cup portion 114 as also shown in dashed lines in FIG. 25. With the finger 130 secured in opening 132, the needle cup 110 provides a complete locked enclosure for the needle point 111 so that inadvertent needle sticks are positively prevented.

To administer an injection with the syringe attached to needle 113, the locking finger 130, if used, is disengaged from opening 132 and the tab 120 is pulled upwardly, i.e., generally transversely to the needle axis A to expose the needle point 111 (FIG. 26). The tab 120 is then pulled in a rearward direction as shown by the arrow 134 in FIG. 26 to unsheath the needle 113 for administration of the injection.

If desired, the safety needle embodiment of FIGS. 25 and 26 may be provided with a cocking or latching mechanism similar to that shown and described above in connection with FIGS. 18-21. An opening (not shown) similar to opening 31 may be provided in tab 120 and a pin (not shown) similar to pin 19 may be provided on the mounting sleeve (not shown) for the needle cup 110 and ribs 118. Operation of this embodiment would then be carried out as shown in FIGS. 19-21 such that when the tab 120 is unlatched from its mounting sleeve, the ribs 118 will return to their unflexed condition and the front cup portion will return to the position shown in FIG. 25 completely enclosing the needle point 111. The locking finger 130, if used, may be engaged in opening 132 to positively lock the cup portions 112, 114 together.

Figure 27:
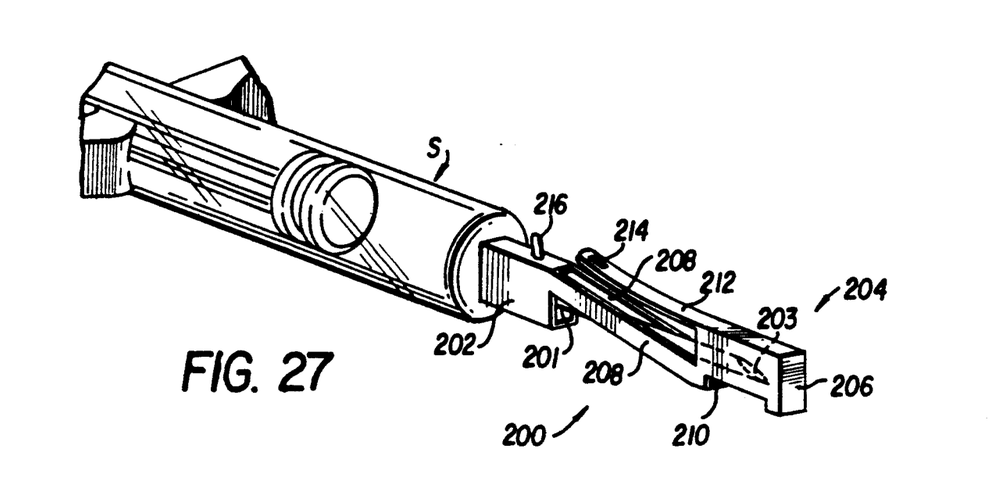
FIG. 27 is a fragmentary perspective view of another alternate embodiment of the invention.

FIG. 27 illustrates another embodiment of the safety needle of the invention attached to a syringe S. In this embodiment a protective sheath 200 encloses a needle 201 and is formed with a generally rectangular cross-section. Sheath 200 comprises a mounting sleeve 202 which engages over a correspondingly shaped hub (not shown) on syringe S. A needle cup 204 having an end cover 206 is connected by a pair of ribs 208 to the mounting sleeve 202. Needle cup 204 encloses needle point 203 and has a needle opening 210 in the lower side thereof through which the needle point 203 extends when the syringe S is used in the manner described below. A tab 212 is integrally formed on the rear side of the needle cup 204 and is provided with an opening 214 engageable with a pin 216 on mounting sleeve 202 so as to provide a latching mechanism similar to that described above in connection with the embodiment of FIGS. 18-21.

In the form shown in FIG. 27, the ribs 208 extend in a generally downward inclination from the upper part of mounting sleeve 202 to the lower part of the needle cup 204. The downward inclination of the ribs 208 advantageously causes the needle cup 204 to translate in a generally downwardly direction when a force is applied to the face of end cover 206, for example, when the end cover 206 is inadvertently brought into contact with a person. Such downward translation of the needle cup 204 locates the needle point 203 in the upper portion of the needle cup in a safer location away from the needle opening 210. Notwithstanding the foregoing, other forms of the ribs 208 are also contemplated, including ribs extending in parallel relationship with the needle axis as shown in FIG. 1.

To administer an injection with the safety needle device shown in FIG. 27, the tab 212 is grasped and pulled upwardly and rearwardly so that the needle point 203 extends through needle opening 210. The opening 214 in tab 212 is then hooked onto pin 216 to latch the protective sheath 200 in a position similar to that shown in FIG. 19. The injection procedure is then carried out in the same manner shown in FIG. 20 and when the needle 201 is withdrawn from the body of the patient, the protective sheath returns to its unflexed condition shown in FIG. 27 with the needle cup 204 protectively enclosing the needle point 203.

Although a certain presently preferred embodiment of the invention has been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What I claim is:

1. A safety needle for insertion into the body of a patient comprising a hypodermic needle having a needle axis and a needle point and being mounted in a needle support, a protective sheath having an axis and comprising a needle cup enclosing the needle point and a mounting sleeve for mounting said sheath to the needle support, flexible means for supporting said needle cup from said mounting sleeve, said flexible means comprising at least two ribs each having two ends, each rib being connected at one end to said mounting sleeve and at the other end to said needle cup, said needle being disposed between said two ribs, said needle cup having a needle opening through which the needle is adapted to pass, said ribs having an unflexed, at rest position and a flexed position such that in the unflexed position the needle axis is misaligned with the needle opening and the ribs are spaced from and disposed substantially parallel to the needle and in the flexed position the needle axis is aligned with the needle opening and the ribs are bowed outwardly away from each other on opposite sides of the needle, said ribs being automatically movable from the flexed position to the unflexed position when the needle is withdrawn from the body of the patient so as to automatically position the needle cup relative to the needle such that the needle axis is misaligned with the needle opening.

2. The safety needle of claim 1, including latching means on said protective sheath for releasably latching the protective sheath in its flexed position with the needle extending at least partly through the needle opening.

3. The safety needle of claim 2, wherein said needle cup has an end cover, said needle opening being disposed in said end cover, said latching means comprising a tab attached to said needle cup, said tab having at least one opening therein, and a pin engageable in said tab opening, said pin being affixed to said mounting sleeve.

4. The safety needle of claim 3, wherein said tab is integrally formed with the needle cup and the pin is integrally formed with the mounting sleeve.

5. The safety needle of claim 2, wherein said latching means comprises a tab attached to said needle cup for manually aligning the needle opening with the needle axis and for manually moving the needle cup so that said needle passes at least partly through the needle opening.

6. The safety needle of claim 5, wherein said tab has at least one opening therein and a pin on said protective sheath for releasably engaging in the tab opening.

7. The safety needle of claim 2, wherein said needle cup has four sides and a rectangular cross-section, said needle opening being disposed in a first side of said needle cup, said latching means comprising a tab attached to a second side of said needle cup opposite said first side.

8. The safety needle of claim 7, wherein said protective sheath comprises a mounting sleeve having a rectangular cross-section, said flexible means comprising at least two ribs connecting a third and fourth sides of said needle cup to said mounting sleeve.

9. The safety needle of claim 8, wherein said ribs extend from said mounting sleeve to said needle cup at an angle relative to the needle axis.

10. The safety needle of claim 1, wherein the axis of the protective sheath is laterally offset from the needle axis to misalign the needle axis with the needle opening.

11. The safety needle of claim 1, including a slot in said needle cup adjacent the opening thereof through which said needle is adapted to pass when said protective sheath is moved from its unflexed position to its flexed position.

12. The safety needle of claim 1, wherein the needle axis is inclined with respect to the axis of the protective sheath to misalign the needle axis with the needle opening.

13. The safety needle of claim 1, wherein said protective sheath is molded of a polymeric material.

14. The safety needle of claim 13, wherein the polymeric material of at least said needle cup is transparent.

15. The safety needle of claim 13, wherein the protective sheath is molded in one piece, said ribs having the same length and a uniform cross-sectional area from end to end.

16. The safety needle of claim 1, including a catheter tube disposed over said needle, said needle opening being a size sufficient for the catheter tube to pass completely through the needle opening.

17. A safety needle comprising a hypodermic needle having a needle axis and a needle point and being mounted in a needle support, a protective sheath surrounding said needle and having an axis misaligned with the needle axis, said sheath comprising a needle cup enclosing the needle point, a mounting sleeve mounting the sheath to the needle support, and at least two flexible ribs each having two ends, each rib being connected at one end to said mounting sleeve and at the other end to said needle cup, said needle cup having a needle opening through which the needle is adapted to pass, said ribs having an unflexed position and a flexed position such that in the unflexed position the ribs are disposed in spaced, substantially parallel relation to the needle and the needle axis is misaligned with the needle opening, and in the flexed position the ribs are bowed outwardly away from the needle and from each other and the needle is aligned with and extends through the needle opening, said ribs being automatically returnable from the flexed position to the unflexed position so as to automatically position the needle cup relative to the needle such that the needle axis is again misaligned with the needle opening.

18. A protective sheath for a hypodermic needle having a needle axis and a needle point and being mounted in a needle support, said sheath comprising a mounting sleeve for mounting the sheath to the needle support, a needle cup adapted to enclose the needle point, said needle cup comprising a front cup portion and a rear cup portion, hinge means for hingedly connecting the cup portions together, at least one flexible rib connecting said mounting sleeve to said rear cup portion, said front cup portion having an end cover adapted to confront the needle point in a first position thereof, a tab connected to said front cup portion for pivoting said front cup portion about the hinge means from said first position away from the rear cup portion to a second position exposing the needle point of said needle.

19. The protective sheath of claim 18, including means for releasably locking said cup portions together.

20. The protective sheath of claim 19, wherein said locking means comprises a finger on one of said cup portions engageable in an opening on the other of said cup portions.

21. The protective sheath of claim 18, including means affixed to and cooperating between said tab and said mounting sleeve for latching said front cup portion in said second position.

22. The protective sheath of claim 18, wherein said protective sheath is molded in one piece from a polymeric material.

23. A method of using a safety needle comprising a hypodermic needle having a needle axis and a needle point and being mounted in a needle support, a protective sheath having an axis and comprising a needle cup enclosing the needle point and a mounting sleeve for mounting the sheath to said needle support, flexible means supporting said needle cup from said mounting sleeve, said flexible means comprising at least two ribs each having two ends, each rib being connected at one end to said mounting sleeve and at the other end to said needle cup such that said needle is disposed between said two ribs, said needle cup having a needle opening through which the needle is adapted to pass, said ribs having an unflexed, at rest position in which the needle axis is misaligned with the needle opening and the ribs are disposed substantially parallel to the needle axis and a flexed position in which the needle axis is aligned with the needle opening and the ribs are outwardly bowed away from each other on opposite sides of the needle, said method comprising the steps of:
  engaging the body of a patient with the needle cup.
  pressing the needle cup against the patient's body in a direction to urge the needle and needle cup relatively of each other until the needle axis is aligned with the needle opening;
  pressing the needle cup against the patient's body in a direction to urge the needle cup axially of the protective sheath to flex the ribs outwardly away from the needle axis and away from one another and move the needle through the needle opening and into the body of the patient; and
  removing the needle from the body of the patient and the needle cup away from contact with the body of the patient to permit the ribs to automatically return to the unflexed, at rest position and automatically misalign the needle axis with the needle opening of the needle cup.

24. The method of claim 23, wherein a catheter tube is disposed over the needle and including the steps of inserting the needle point into a blood vessel in the body of the patient and sliding the catheter tube axially off the needle and into the blood vessel and removing the needle and protective sheath from the body while leaving the catheter tube in the blood vessel.

25. A method of using a safety needle comprising a hypodermic needle having a needle axis and a needle point and being mounted in a needle support, a protective sheath having an axis and comprising a needle cup enclosing the needle point and a mounting sleeve for mounting the sheath to said needle support, flexible means supporting said needle cup from said mounting sleeve, said flexible means comprising at least two ribs each having two ends, each rib being connected at one end to said mounting sleeve and at the other end to said needle cup such that said needle is disposed between said two ribs, said needle cup having a needle opening through which the needle is adapted to pass, said ribs having an unflexed, at rest position in which the needle axis is misaligned with the needle opening and the ribs are disposed substantially parallel to the needle axis and a flexed position in which the needle axis is aligned with the needle opening and the ribs are outwardly bowed away from each other on opposite side of the needle, a tab attached to the needle cup and having an opening and a pin attached to the protective sheath, said method comprising the steps of:

grasping the tab;

manually moving the needle cup with the tab until the needle passes through the needle opening to expose the needle;

engaging the pin with the tab opening to releasably retain the needle exposed;

inserting the needle in the body of a patient;

engaging the body of the patient with the needle cup to thereby release the pin from the tab opening; and withdrawing the needle from the patient's body and the needle cup away from contact with the body of the patient to permit the ribs to automatically return to the unflexed, at rest position and automatically misalign the needle axis with the needle opening of the needle cup.

26. The method of claim 25, wherein a catheter tube is disposed over the needle and including the steps of inserting the needle point into a blood vessel in the body of the patient and sliding the catheter tube axially off the needle and into the blood vessel and removing the needle and protective sheath from the body while leaving the catheter tube in the blood vessel.

* * * * *